(12) United States Patent
Polyak et al.

(10) Patent No.: US 7,465,553 B2
(45) Date of Patent: Dec. 16, 2008

(54) PSORIASIN EXPRESSION BY BREAST EPITHELIAL CELLS

(75) Inventors: Kornelia Polyak, Brookline, MA (US); Charlotta Enerbäck, Gothenburg (SE)

(73) Assignee: Dana-Farber Cancer Institute, Inc., Boston, MA (US)

( * ) Notice: Subject to any disclaimer, the term of this patent is extended or adjusted under 35 U.S.C. 154(b) by 431 days.

(21) Appl. No.: 10/331,200

(22) Filed: Dec. 30, 2002

(65) Prior Publication Data

US 2003/0138833 A1    Jul. 24, 2003

Related U.S. Application Data

(60) Provisional application No. 60/345,740, filed on Dec. 31, 2001.

(51) Int. Cl.
*G01N 33/536* (2006.01)
(52) U.S. Cl. ............ 435/7.23; 435/6; 436/501; 436/518
(58) Field of Classification Search .......... 435/7.1
See application file for complete search history.

(56) References Cited

FOREIGN PATENT DOCUMENTS

| WO | WO 00/26668 | 5/2000 |
|----|-------------|--------|
| WO | WO 00/55629 | 9/2000 |
| WO | WO 01/87238 | 11/2001 |

OTHER PUBLICATIONS

Filella et al. Prostate-specific antigen detection by ultrasensitive assay in sample from women. Dec. 1999. Prostate 29(5):311-316.*
Hillebrand et al. Serum-to-urinary prostate-specific antigen ratio in patients with benign prostatic hyperplaysia and prostate cancer. Nov.-Dec. 2000. Anticancer Research 20(6D):4995-6.*
Al-Haddad et al. Psoriasin (S100A7) expression and invasive breast cancer. Dec. 1999. American Journal of Pathology 155(6):2057-2066.*
Leygue et al., "Differential Expression of Psoriasin Messenger RNA between in Situ and Invasive Human Breast Carcinoma", Cancer Res. 56:4606-4609 (1996).
Porter et al., "A SAGE (Serial Analysis of Gene Expression) View of Breast Tumor Progression", Cancer Res. 61:5697-5702 (2001).
Watson et al., "Molecules in focus Psoriasin (S100A7)", Intl. J. Biochem & Cell Biol. 30:567-571 (1998).
Al-Haddad et al., "Psoriasin (S100A7) expression and invasive breast cancer", The Am. J. Pathol., 155(6):2057-2066 (Dec. 1999).
Fisher et al., "Pathologic Findings from the national Surgical Adjuvant Breast Project (NSABP) Eight-Year Update of Protocol B-17", Cancer, 86(3):429-438 (1999).
Cancer Topics: Ductal Carcinoma In Situ, Website of the National Cancer institute of the U.S. National Instututes of Health (http://www.cacer.gov/cancertopics/pdq/treatment/breast/HealthProfessional/page5).

* cited by examiner

*Primary Examiner*—Misook Yu
(74) *Attorney, Agent, or Firm*—Fish & Richardson P.C.

(57) ABSTRACT

The invention features methods of diagnosing high grade ductal carcinoma in situ (DCIS) These methods involve measuring: (1) the level of HID-5 in a body fluid (e.g., blood or urine) of a subject suspected of having, or at risk of having, high grade DCIS; or (2) the level of HID-5 gene expression in breast tissue from a subject suspected of having, or at risk of having, high grade DCIS. The invention also embodies a method of inhibiting expression of HID-5 protein in DCIS cells and methods of treating a subject suspected of having, or at risk of having, high grade DCIS.

5 Claims, 7 Drawing Sheets

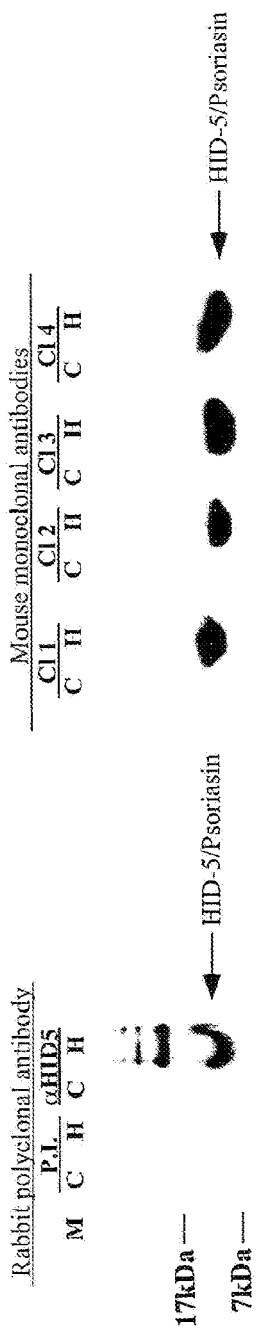
FIG. 2A
FIG. 2C
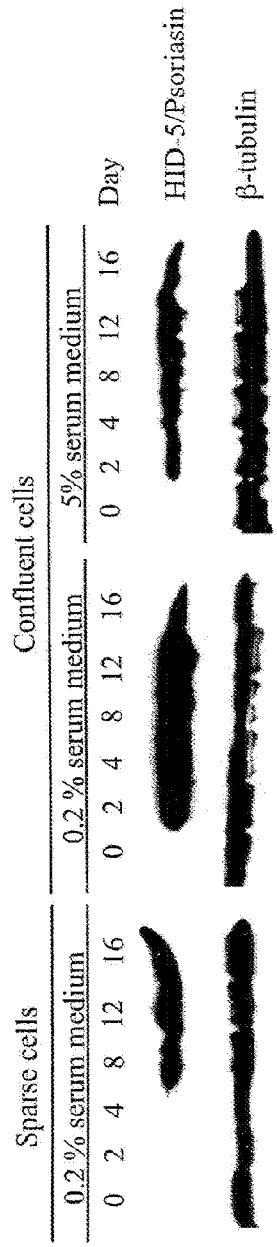
FIG. 2B
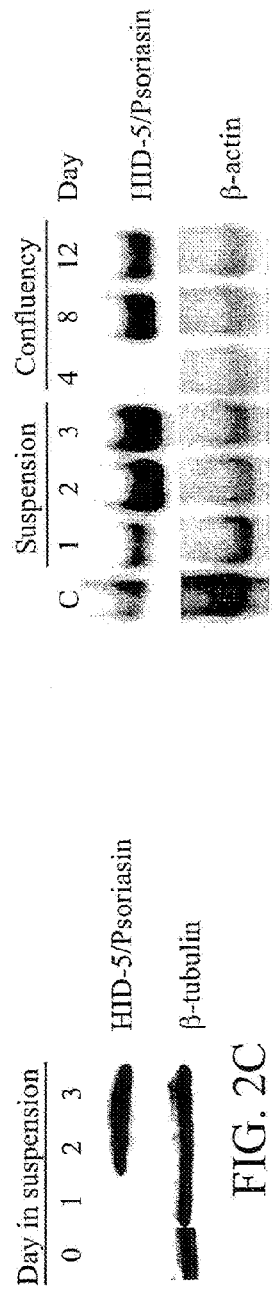
FIG. 2D

MSNTQAERSIIGMIDMFHKYTRRDDKIDKPSLLTMMKENFPNFLSACDKKGTNYLADVFEKKDKNEDKKID
FSEFLSLLGDIATDYHKQSHGAAPCSGGSQ

FIG. 4A atgagcaacactcaagctgagaggtccataataggcatgatcgacatgtttcacaaatacaccagacgtga
tgacaagattgacaagcctgctgacgatgaaggagaacttcccaacttccttagtgcctgtg
acaaaagggcacaaattacctcgccgacgtctttgagaaaaggacaagaatgaggataagaagatgat
ttttctgagtttctgtcctttgctgggagacatagccacagccacaagcagacagcagcgcc
ctgttccggggggcagccag

FIG. 4B

SEQUENCE LISTING

```
<160> NUMBER OF SEQ ID NOS: 12

<210> SEQ ID NO 1
<211> LENGTH: 101
<212> TYPE: PRT
<213> ORGANISM: Homo sapiens

<400> SEQUENCE: 1

Met Ser Asn Thr Gln Ala Glu Arg Ser Ile Ile Gly Met Ile Asp Met
 1               5                  10                  15

Phe His Lys Tyr Thr Arg Arg Asp Asp Lys Ile Asp Lys Pro Ser Leu
            20                  25                  30

Leu Thr Met Met Lys Glu Asn Phe Pro Asn Phe Leu Ser Ala Cys Asp
        35                  40                  45

Lys Lys Gly Thr Asn Tyr Leu Ala Asp Val Phe Glu Lys Lys Asp Lys
    50                  55                  60

Asn Glu Asp Lys Lys Ile Asp Phe Ser Glu Phe Leu Ser Leu Leu Gly
65                  70                  75                  80
```

```
Asp Ile Ala Thr Asp Tyr His Lys Gln Ser His Gly Ala Ala Pro Cys
              85                  90                  95

Ser Gly Gly Ser Gln
            100

<210> SEQ ID NO 2
<211> LENGTH: 303
<212> TYPE: DNA
<213> ORGANISM: Homo sapiens
<220> FEATURE:
<221> NAME/KEY: CDS
<222> LOCATION: (1)...(303)

<400> SEQUENCE: 2 atg agc aac act caa gct gag agg tcc ata ata ggc atg atc gac atg      48
Met Ser Asn Thr Gln Ala Glu Arg Ser Ile Ile Gly Met Ile Asp Met
 1               5                  10                  15 ttt cac aaa tac acc aga cgt gat gac aag att gac aag cca agc ctg      96
Phe His Lys Tyr Thr Arg Arg Asp Asp Lys Ile Asp Lys Pro Ser Leu
                20                  25                  30 ctg acg atg atg aag gag aac ttc ccc aac ttc ctt agt gcc tgt gac     144
Leu Thr Met Met Lys Glu Asn Phe Pro Asn Phe Leu Ser Ala Cys Asp
            35                  40                  45 aaa aag ggc aca aat tac ctc gcc gac gtc ttt gag aaa aag gac aag     192
Lys Lys Gly Thr Asn Tyr Leu Ala Asp Val Phe Glu Lys Lys Asp Lys
         50                 55                  60 aat gag gat aag aag att gat ttt tct gag ttt ctg tcc ttg ctg gga     240
Asn Glu Asp Lys Lys Ile Asp Phe Ser Glu Phe Leu Ser Leu Leu Gly
 65                  70                  75                  80 gac ata gcc aca gac tac cac aag cag agc cat gga gca gcg ccc tgt     288
Asp Ile Ala Thr Asp Tyr His Lys Gln Ser His Gly Ala Ala Pro Cys
             85                  90                  95 tcc ggg ggc agc cag                                                 303
Ser Gly Gly Ser Gln
            100

<210> SEQ ID NO 3
<211> LENGTH: 18
<212> TYPE: PRT
<213> ORGANISM: Homo sapiens

<400> SEQUENCE: 3

Thr Asp Tyr His Lys Gln Ser His Gly Ala Ala Pro Cys Ser Gly Gly
 1               5                  10                  15

Ser Gln

<210> SEQ ID NO 4
<211> LENGTH: 10
<212> TYPE: DNA
<213> ORGANISM: Homo sapiens

<400> SEQUENCE: 4
gagcagcgcc                                                          10

<210> SEQ ID NO 5
<211> LENGTH: 10
<212> TYPE: DNA
<213> ORGANISM: Homo sapiens

<400> SEQUENCE: 5
gtggccacgg                                                          10
```

```
<210> SEQ ID NO 6
<211> LENGTH: 10
<212> TYPE: DNA
<213> ORGANISM: Homo sapiens

<400> SEQUENCE: 6
tgttctggag                                                              10

<210> SEQ ID NO 7
<211> LENGTH: 10
<212> TYPE: DNA
<213> ORGANISM: Homo sapiens

<400> SEQUENCE: 7
tggaagcact                                                              10

<210> SEQ ID NO 8
<211> LENGTH: 10
<212> TYPE: DNA
<213> ORGANISM: Homo sapiens

<400> SEQUENCE: 8
cgaatgtcct                                                              10

<210> SEQ ID NO 9
<211> LENGTH: 10
<212> TYPE: DNA
<213> ORGANISM: Homo sapiens

<400> SEQUENCE: 9
ctatagcata                                                              10

<210> SEQ ID NO 10
<211> LENGTH: 10
<212> TYPE: DNA
<213> ORGANISM: Homo sapiens

<400> SEQUENCE: 10
ggcacctcag                                                              10

<210> SEQ ID NO 11
<211> LENGTH: 10
<212> TYPE: DNA
<213> ORGANISM: Homo sapiens

<400> SEQUENCE: 11
gtggcccacg                                                              10

<210> SEQ ID NO 12
<211> LENGTH: 10
<212> TYPE: DNA
<213> ORGANISM: Homo sapiens

<400> SEQUENCE: 12
cctgtaatcc                                                              10
```

PSORIASIN EXPRESSION BY BREAST EPITHELIAL CELLS

This application claims priority of U.S. Provisional Application No. 60/345,740, filed Dec. 31, 2001, the disclosure of which is incorporated herein by reference in its entirety.

STATEMENT REGARDING FEDERALLY SPONSORED RESEARCH OR DEVELOPMENT

The research described in this application was supported in part by a grant (No. P50 CA89393-01) from the National Cancer Institute of the National Institutes of Health. Thus the government has certain rights in the invention.

TECHNICAL FIELD

This invention relates to cancer diagnosis and treatment, and more particularly to breast cancer treatment and diagnosis.

BACKGROUND

Breast carcinoma is the second leading cause of cancer-related death in women of the western world. In the United States alone over 175,000 new cases are diagnosed annually. The natural history of breast cancer involves a sequential progression through defined clinical and pathologic stages starting with initially benign then atypical hyperproliferation, progressing into in situ then invasive carcinomas, and culminating in metastatic disease. Ductal carcinoma in situ (DCIS) is the precursor of invasive ductal carcinoma. Thus, it is important that there be a reliable test for DCIS.

SUMMARY

The invention is based on the observation that human high grade DCIS cells express elevated levels of a protein designated by the inventors HID-5 (high in DCIS-5). This protein is also known as psoriasin. Low and intermediate DCIS express the HID-5 gene at a very low level, if at all. In addition, the inventors discovered that HID-5 is secreted by breast cancer cells. Thus, the invention features methods of diagnosing and treating high grade DCIS.

More specifically, the invention features a method of diagnosis. The method involves: (a) identifying a subject suspected of having or at risk of having high-grade ductal carcinoma in situ (DCIS); and (b) measuring the level of psoriasin in a sample of a body fluid (e.g., blood or urine), a lavage (e.g., a breast duct lavage), or an aspirate (e.g., a nipple aspirate) from the subject. An elevated level of psoriasin in the sample, compared to a control level of psoriasin, is an indication that the subject has high grade DCIS.

Also included in the invention is a method of diagnosis. The method involves: (a) identifying a subject suspected of having or at risk of having high-grade ductal carcinoma in situ (DCIS); and (b) determining the level of psoriasin gene expression in a sample of breast tissue from the subject. An elevated level of psoriasin gene expression in the sample, compared to a control level of psoriasin gene expression, is an indication that the subject has high grade DCIS. The level of psoriasin gene expression can be determined as a function of either the level of psoriasin in the sample of breast tissue or the level of psoriasin mRNA in the sample of breast tissue.

Another aspect of the invention is a method of inhibiting expression of psoriasin in a ductal carcinoma in situ (DCIS) cell. This method involves introducing into the cell an antisense oligonucleotide that hybridizes to a psoriasin transcript, the antisense oligonucletide inhibiting expression of psoriasin in the cell. The introducing step can involve: (a) administration of the antisense oligonucleotide to the cell and uptake of the antisense oligonucleotide by the cell; or (b) administering to the cell a nucleic acid comprising a transcriptional regulatory element (TRE) operably linked to a nucleotide sequence complementary to the antisense oligonucleotide, transcription of the nucleotide sequence inside the cell producing the antisense oligonucleotide. The cell can be in a mammal, e.g. a human.

Also embraced by the invention is a method of inhibiting progression of high-grade ductal carcinoma in situ (DCIS) in a subject. The method involves: (a) identifying a subject suspected of having or at risk of having high-grade ductal carcinoma in situ (DCIS); and (b) administering to the subject an psoriasin-binding agent. The psoriasin-binding agent can be, for example, an antibody that binds to psoriasin.

Also featured by the invention is a method of discriminating high-grade DCIS from intermediate grade DCIS or low grade DCIS. The method involves: (a) providing a sample of breast tissue from a subject identified as having DCIS; and (b) testing for psoriasin in the sample. A detectable level of psoriasin in the sample is an indication that the subject has high-grade DCIS.

In yet another aspect of the invention is a method of identifying psoriasin-binding agents. The method involves: (a) providing a sample comprising psoriasin; (b) contacting the sample with a test agent; and (c) determining whether the test agent binds to the psoriasin. In this method, the test agent is not an antibody.

The invention also embraces a method of inhibiting apoptosis. The method involves: (a) identifying (i) cells at risk for apoptosis, or (ii) a subject having cells at risk for apoptosis; and (b) administering psoriasin to the cells. The psoriasin can be administered by delivering to the cells or to the vicinity of the cells: (a) a nucleic acid that encodes psoriasin; or (b) purified psoriasin. Alternatively, the psoriasin can be administered by introducing into the vicinity of the cells a recombinant cell (1) transfected with a nucleic acid encoding psoriasin and (2) secreting psoriasin.

The invention features, in addition, a method of making a cell more susceptible to apoptosis. The method involves: (a) identifying a cell as a target for apoptosis; and (b) administering to the cell a psoriasin-binding agent. The cell can be within a mammal and the agent can be an antibody. The method can further involve administering to the cell a second agent that promotes apoptosis in a susceptible cell.

In another aspect, the invention includes a screening method. The method involves: (a) identifying a subject as having breast cancer; and (b) testing for the presence, in a sample of a body fluid (e.g., blood), a lavage, or an aspirate from the subject, of an antibody that bind to psoriasin. The presence of an antibody in the sample is an indication that the subject is a potential candidate for vaccination with HID-5 or a peptide fragment or HID-5.

Unless otherwise defined, all technical and scientific terms used herein have the same meaning as commonly understood by one of ordinary skill in the art to which this invention pertains. In case of conflict, the present document, including definitions, will control. Preferred methods and materials are described below, although methods and materials similar or equivalent to those described herein can be used in the practice or testing of the present invention. All publications, patent applications, patents and other references mentioned herein are incorporated by reference in their entirety. The materials, methods, and examples disclosed herein are illustrative only and not intended to be limiting.

Other features and advantages of the invention, e.g., diagnosing high grade DCIS, will be apparent from the following description, from the drawings and from the claims.

DESCRIPTION OF DRAWINGS

FIG. 2A is a pair of photographs of immunoblots showing the specificity of a polyclonal anti-HID-5 antibody (left panel) and four individual monoclonal anti-HID-5 antibodies (right panel). Lysates of HID-5-expressing ("H") and control HID-5-non-expressing ("C") cells were resolved by sodium dodecyl sulfate polyacrylamide gel electrophoresis (SDS-PAGE) and the resulting gels were blotted onto membranes that were stained with control pre-immune serum ("P.I."), polyclonal anti-HID-5 antibody ("αHID5"), or the four monoclonal anti-HID-5 antibodies ("Cl 1", "Cl 2", "Cl 3", and "Cl 4"). The lane labeled "M" shows the positions of 17 kDa and 7 kDa molecular weight markers. The positions of HID-5 in both panels are indicated ("HID-5/Psoriasin").

FIG. 2B is a series of three photographs of immunoblots showing the relative levels of HID-5 protein expression by MCF10A cells grown in culture medium containing a low ("0.2% serum medium") or high ("5% serum medium") concentration of serum and under confluent ("Confluent cells") or sparse ("Sparse cells") culture conditions. Cells were tested for HID-5 protein expression after 0, 2, 4, 8, 12, and 16 days in culture. The blots were generated as described for FIG. 2A and stained with a polyclonal antibody specific for HID-5. The positions of HID-5 ("HID-5/Psoriasin") and a control protein ("β-tubulin") on the immunoblots are indicated.

FIG. 2C is a photograph of an immunoblot showing the relative levels of HID-5 protein expressed by MCF10A cells grown in suspension culture for 0, 1, 2, and 3 days. The blots were generated as described for FIG. 2A and stained with a polyclonal antibody specific for HID-5. The positions of HID-5 ("HID-5/Psoriasin") and a control protein ("β-tubulin") on the imnmunoblot are indicated.

FIG. 2D is a photograph of an autoradiogram from a Northern blot showing the relative levels of HID-5 mRNA expressed by MCF10A cells grown in suspension culture ("Suspension") for 1, 2, and 3 days or confluent culture conditions ("Confluency") for 4, 8, and 12 days. RNA was isolated from the cells at the indicated times and the RNA was subjected to Northern blot analysis as previously described [Krop et al. (2001) Proc. Natl. Acad. Sci., U.S.A. 98:9796-9801]. The blots were analyzed sequentially with $^{32}$P-labeled HID-5 and β-actin cDNA probes and the positions of HID-5 ("HID-5/Psoriasin") and β-actin on the blots are shown.

FIG. 4A is a depiction of the amino acid sequence (SEQ ID NO:1) of HID-5/psoriasin.

FIG. 4B is a depiction of nucleotide sequence (SEQ ID NO:2) of HID-5/psoriasin.

DETAILED DESCRIPTION

Figure 1A:
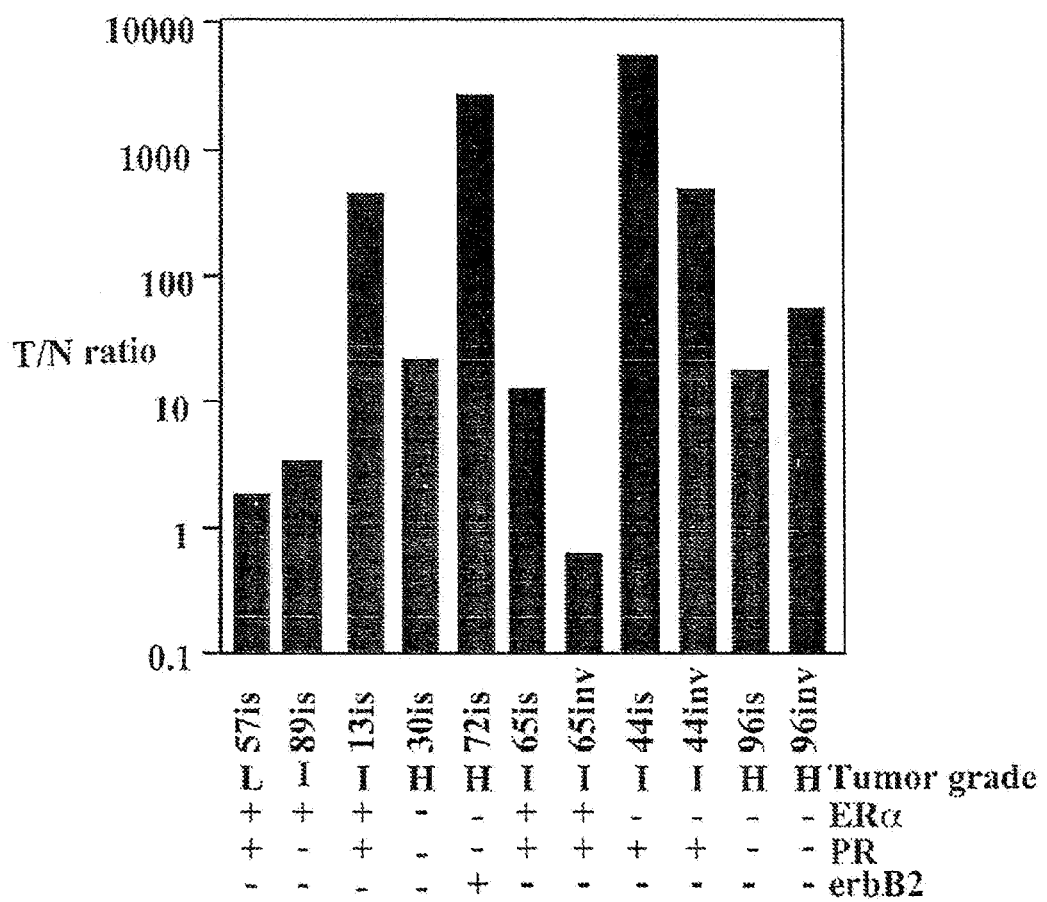
FIG. 1A is a bar graph showing the results of a real-time PCR analysis of HID-5/psoriasin mRNA expression in laser capture microdissection (LCM) purified primary breast carcinomas and corresponding normal breast epithelium. The data are expressed as the ratio of the HID-5/psoriasin mRNA level in cancerous epithelium to the HID-5/psoriasin mRNA level in the corresponding normal epithelium ("T/N ratio"). Each bar is labeled with the case number and acronym indicating whether the carcinoma was in situ ("is") or invasive ("inv"). Whether the carcinoma was high ("H"), intermediate ("I"), or low ("L") grade and expression ("+") and lack of expression ("−") of estrogen receptor a ("ERα"), progesterone receptor ("PR"), and erbB2 are shown.

The inventors discovered by Serial Analysis of Gene Expression (SAGE) that HID-5/psoriasin is differentially and highly expressed in high grade DCIS cells relative to normal breast epithelium and intermediate grade DCIS. Chromosome spread and interphase nuclear FISH analysis indicated that the increased expression of HID-5 in the high grade DCIS cells was not due to gene amplification. A real time PCR analysis of a panel of primary breast cancers indicated the presence of higher levels of HID-5 mRNA in high and intermediate grade tumors than in normal mammary epithelium from the same patient. By mRNA in situ hybridization, HID-5 mRNA was detected in cells of high grade but not low or intermediate grade DCIS cells or normal mammary epithelium.

In vitro experiments with normal mammary epithelial MCF10A cells indicated that: (a) HID-5 protein expression was greatly up-regulated by growing the cells in medium containing a low concentration of serum, under confluent conditions and in suspension; and (b) HID-5 mRNA expression was greatly up-regulated by growing the cells under confluent conditions and in suspension. Since serum deprivation, confluency and lack of cell anchorage also resulted in G1 arrest and apoptosis, cells surviving these conditions are likely to be relatively resistant to apoptosis. Thus HID-5 is likely involved in regulation of G1 arrest and relative resistance to apoptosis.

Nuclear and cytoplasmic staining by HID-5-specific antibody was seen in MDA-MB-468 breast cancer cells and serum deprived MCF10A cells. Moreover testing of cell lysates and culture medium of MDA-MB-468 cells indicated that HID-5 is both expressed intracellularly and secreted.

Immunochemical analyses indicated enhanced expression of HID-5 in a significant number of high grade breast cancers versus low and intermediate grade breast cancers and normal mammary epithelium.

These data provide the bases for the following methods of the invention

Diagnostic Assays

The invention features diagnostic assays. Such assays are based on the findings that: (1) high grade DCIS cells express high levels of HID-5 protein and HID-5 mRNA while normal breast cells and low and intermediate grade breast cancer cells express either significantly lower levels or undetectable levels of HID-5 protein and HID-5 mRNA; and (2) HID-5 protein is secreted by breast cancer cells. These findings provide the bases for assays to diagnose high grade DCIS. Such assays can be used on their own or, preferably, in conjunction with other procedures to test for high grade DCIS.

In the assays of the invention either: (1) the presence of HID-5 protein or HID-5 mRNA in is tested for or their levels are measured; or (2) the level of HID-5 protein is measured in a liquid sample such as a body fluid (e.g., urine, saliva, semen, blood, or serum or plasma derived from blood); a lavage such as a breast duct lavage, lung lavage, a gastric lavage, a rectal or colonic lavage, or a vaginal lavage; an aspirate such as a nipple aspirate; or a fluid such as a supernatant from a cell culture. In order to test for the presence, or measure the level, of HID-5 mRNA in cells, the cells can be lysed and total RNA can be purified or semi-purified from lysates by any of a variety of methods known in the art. Methods of detecting or measuring levels of particular mRNA transcripts are also familiar to those in the art. Such assays include, without limitation, hybridization assays using detectably labeled HID-5-specific DNA or RNA probes and quantitative or semi-quantitative RT-PCR methodologies employing appropriate HID-5-specific oligonucleotide primers. Additional methods for quantitating mRNA in cell lysates include RNA protection assays and serial analysis of gene expression (SAGE). Alternatively, qualitative, quantitative, or semi-quantitative in situ hybridization assays can be carried out using, for example, tissue sections or unlysed cell suspensions, and detectably (e.g., fluorescently or enzyme) labeled DNA or RNA probes.

Methods of detecting or measuring the levels of a protein of interest (e.g., HID-5) in cells are known in the art. Many such methods employ antibodies (e.g., polyclonal antibodies or mAbs) that bind specifically to the protein. In such assays, the antibody itself or a secondary antibody that binds to it can be detectably labeled. Alternatively, the antibody can be conjugated with biotin, and detectably labeled avidin (a protein that binds to biotin) can be used to detect the presence of the biotinylated antibody. Combinations of these approaches (including "multi-layer" assays) familiar to those in the art can be used to enhance the sensitivity of assays. Some of these assays (e.g., immunohistological methods or fluorescence flow cytometry) can be applied to histological sections or unlysed cell suspensions. The methods described below for detecting HID-5 in a liquid sample can also be used to detect HID-5 in cell lysates.

Methods of detecting HID-5 in a liquid sample (see above) basically involve contacting a sample of interest with an antibody that binds to HID-5 and testing for binding of the antibody to a component of the sample. In such assays the antibody need not be detectably labeled and can be used without a second antibody that binds to HID-5. For example, by exploiting the phenomenon of surface plasmon resonance, an antibody specific for HID-5 bound to an appropriate solid substrate is exposed to the sample. Binding of HID-5 to the antibody on the solid substrate results in a change in the intensity of surface plasmon resonance that can be detected qualitatively or quantitatively by an appropriate instrument, e.g., a Biacore apparatus (Biacore International AB, Rapsgatan, Sweden).

Moreover, assays for detection of HID-5 in a liquid sample can involve the use, for example, of: (a) a single HID-5-specific antibody that is detectably labeled; (b) an unlabeled HID-5-specific antibody and a detectably labeled secondary antibody; or (c) a biotinylated HID-5-specific antibody and detectably labeled avidin. In addition, as described above for detection of proteins in cells, combinations of these approaches (including "multi-layer" assays) familiar to those in the art can be used to enhance the sensitivity of assays. In these assays, the sample or an (aliquot of the sample) suspected of containing HID-5 can be immobilized on a solid substrate such as a nylon or nitrocellulose membrane by, for example, "spotting" an aliquot of the liquid sample or by blotting of an electrophoretic gel on which the sample or an aliquot of the sample has been subjected to electrophoretic separation. The presence or amount of HID-5 on the solid substrate is then assayed using any of the above-described forms of the HID-5-specific antibody and, where required, appropriate detectably labeled secondary antibodies or avidin.

The invention also features "sandwich" assays. In these sandwich assays, instead of immobilizing samples on solid substrates by the methods described above, any HID-5 that may be present in a sample can be immobilized on the solid substrate by, prior to exposing the solid substrate to the sample, conjugating a second ("capture") HID-5-specific antibody (polyclonal or mAb) to the solid substrate by any of a variety of methods known in the art. In exposing the sample to the solid substrate with the second HID-5-specific antibody bound to it, any HID-5 in the sample (or sample aliquot) will bind to the second HID-5-specific antibody on the solid substrate. The presence or amount of HID-5 bound to the conjugated second HID-5-specific antibody is then assayed using a "detection" HID-5-specific antibody by methods essentially the same as those described above using a single HID-5-specific antibody. It is understood that in these sandwich assays, the capture antibody should not bind to the same epitope (or range of epitopes in the case of a polyclonal antibody) as the detection antibody. Thus, if a mAb is used as a capture antibody, the detection antibody can be either: (a) another mAb that binds to an epitope that is either completely physically separated from or only partially overlaps with the epitope to which the capture mAb binds; or (b) a polyclonal antibody that binds to epitopes other than or in addition to that to which the capture mAb binds. On the other hand, if a polyclonal antibody is used as a capture antibody, the detection antibody can be either (a) a mAb that binds to an epitope to that is either completely physically separated from or partially overlaps with any of the epitopes to which the capture polyclonal antibody binds; or (b) a polyclonal antibody that binds to epitopes other than or in addition to that to which the capture polyclonal antibody binds. Assays which involve the used of a capture and detection antibody include sandwich ELISA assays, sandwich Western blotting assays, and sandwich immunomagnetic detection assays.

Suitable solid substrates to which the capture antibody can be bound include, without limitation, the plastic bottoms and sides of wells of microtiter plates, membranes such as nylon or nitrocellulose membranes, polymeric (e.g., without limitation, agarose, cellulose, or polyacrylamide) beads or particles. It is noted that HID-5-specific antibodies bound to such beads or particles can also be used for immunoaffinity purification of HID-5.

Methods of detecting or for quantifying a detectable label depend on the nature of the label and are known in the art. Appropriate labels include, without limitation, radionuclides (e.g., $^{125}$I, $^{131}$I, $^{35}$S, $^{3}$H, $^{32}$P, $^{33}$P, or $^{14}$C), fluorescent moieties (e.g., fluorescein, rhodamine, or phycoerythrin), luminescent moieties (e.g., Qdot™ nanoparticles supplied by the Quantum Dot Corporation, Palo Alto, Calif.), compounds that absorb light of a defined wavelength, or enzymes (e.g., alkaline phosphatase or horseradish peroxidase). The products of reactions catalyzed by appropriate enzymes can be, without limitation, fluorescent, luminescent, or radioactive or they may absorb visible or ultraviolet light. Examples of detectors include, without limitation, x-ray film, radioactivity counters, scintillation counters, spectrophotometers, colorimeters, fluorometers, luminometers, and densitometers.

In assays to diagnose high grade DCIS, the concentration of HID-5 in, for example, serum from a patient suspected of having, or at risk of having, high grade DCIS is compared to the mean of the concentrations of HID-5 in sera from a control group of subjects, e.g., subjects not having breast cancer, subjects having low grade breast cancer, subjects having intermediate grade breast cancer, or any combination of such subjects. A significantly higher concentration of HID-5 in the serum of the patient relative to the mean concentration in sera of the control group would indicate that the patient has high grade DCIS. Alternatively, if a sample of the subject's serum that was obtained at a prior date at which the patient clearly did not have breast cancer is available, the concentration of HID-5 in the test serum sample can be compared to the concentration in the prior obtained sample. A higher level in the test serum sample would be an indication that the patient had high grade DCIS.

It is understood that, while the above descriptions of the diagnostic assays refer to assays on serum, the assays can also be carried out on any of the other fluid samples listed herein. In addition, it is noted that the patients and control subjects referred to above need not be human patients. They can be for example, non-human primates (e.g., monkeys), horses, sheep, cattle, goats, pigs, dogs, guinea pigs, hamsters, rats, rabbits or mice.

It is understood that, since the SAGE analysis described in Example 2 showed that expression of calgranulin B/S100A9 and connexin 43 was upregulated in high grade DCIS cells relative to normal breast epithelial cells and intermediate grade DCIS cells, detection and/or measurement of calgranulin B/S100A9 or connexin 43 expression by test breast cells, by adaption of any of the above-described methods, can be performed to diagnose high grade DCIS.

The data described below show that the expression of HID-5 is upregulated in certain breast cancer patients. Thus, in patients that have the ability to mount an autoimmune response to HID-5, immunization with HID-5 or one or more peptide fragments of HID-5 could be an effective immunotherapeutic regimen. Without being limited to any particular mechanism of action, therapeutic effect in such a regimen could be due to the action of cytotoxic T lymphocytes (CTL) specific for HID-5 peptide fragments or neutralizing antibodies specific for HID-5. Thus, the invention also features a method of screening a breast cancer patient for the presence of antibodies specific for HID-5, wherein the presence of HID-5-specific antibodies indicates that the patient could benefit from HID-5-specific immunotherapy. Methods to test for the presence of antibodies are known in art and include obvious modifications of some of the above-described assays to test for HID-5. In such assays, a sample from a subject (e.g., any of the above-listed body fluids, ravages, or aspirates) is contacted with HID-5, or a fragment of HID-5, and binding of antibody to the HID-5, or fragment of HID-5, is tested using any of the detection methods recited above.

Methods of Inhibiting Expression of HID-5 in a Cell

Also included in the invention are methods of inhibiting expression of HID-5 in cells. One such method involves introducing into a cell (a) an antisense oligonucleotide or (b) a nucleic acid comprising a transcriptional regulatory element (TRE) operably linked to a nucleic sequence that is transcribed in the cell into an antisense RNA. The antisense oligonucleotide and the antisense RNA hybridize to an HID-5 transcript and have the effect in the cell of inhibiting expression of HID-5 in the cell. Inhibiting HID-5 expression in the cell can inhibit proliferation and/or survival of the cell. The method can thus be useful in inhibiting proliferation and/or survival of a cancer cell (e.g., a breast cancer cell) and can be applied to the therapy of cancer. The method can be used, for example, in the treatment of high grade breast cancer, e.g., high grade DCIS or high grade invasive breast cancer.

Antisense compounds are generally used to interfere with protein expression either by, for example, interfering directly with translation of a target mRNA molecule, by RNAse-H-mediated degradation of the target mRNA, by interference with 5' capping of mRNA, by prevention of translation factor binding to the target mRNA by masking of the 5' cap, or by inhibiting of mRNA polyadenylation. The interference with protein expression arises from the hybridization of the antisense compound with its target mRNA. A specific targeting site on a target mRNA of interest for interaction with an antisense compound is chosen. Thus, for example, for modulation of polyadenylation a preferred target site on an mRNA target is a polyadenylation signal or a polyadenylation site. For diminishing mRNA stability or degradation, destabilizing sequence are preferred target sites. Once one or more target sites have been identified, oligonucleotides are chosen which are sufficiently complementary to the target site (i.e., hybridize sufficiently well under physiological conditions and with sufficient specificity) to give the desired effect.

With respect to this invention, the term "oligonucleotide" refers to an oligomer or polymer of RNA, DNA, or a mimetic of either. The term includes oligonucleotides composed of naturally-occurring nucleobases, sugars, and covalent intemucleoside (backbone) linkages. The normal linkage or backbone of RNA and DNA is a 3' to 5' phosphodiester bond. The term also refers however to oligonucleotides composed entirely of, or having portions containing, non-naturally occurring components which function in a similar manner to the oligonucleotides containing only naturally-occurring components. Such modified substituted oligonucleotides are often preferred over native forms because of desirable properties such as, for example, enhanced cellular uptake, enhanced affinity for target sequence, and increased stability in the presence of nucleases. In the mimetics, the core base (pyrimidine or purine) structure is generally preserved but (1) the sugars are either modified or replaced with other components and/or (2) the inter-nucleobase linkages are modified. One class of nucleic acid mimetic that has proven to be very useful is referred to as protein nucleic acid (PNA). In PNA molecules the sugar backbone is replaced with an amide-containing backbone, in particular an aminoethylglycine backbone. The bases are retained and are bound directly to the aza nitrogen atoms of the amide portion of the backbone. PNA and other mimetics useful in the instant invention are described in detail in U.S. Pat. No. 6,210,289.

The antisense oligomers to be used in the methods of the invention generally comprise about 8 to about 100 (e.g., about 14 to about 80 or about 14 to about 35) nucleobases (or nucleosides where the nucleobases are naturally occurring).

The antisense oligonucleotides can themselves be introduced into a cell or an expression vector containing a nucleic sequence (operably linked to a TRE) encoding the antisense oligonucleotide can be introduced into the cell. In the latter case, the oligonucleotide produced by the expression vector is an RNA oligonucleotide and the RNA oligonucleotide will be composed entirely of naturally occurring components.

The methods of the invention can be in vitro or in vivo. In vitro applications of the methods can be useful, for example, in basic scientific studies on cell proliferation or cell survival. In such in vitro methods, appropriate cells (e.g., those expressing HID-5), can be incubated for various lengths of time with (a) the antisense oligonucleotides or (b) expression vectors containing nucleic acid sequences encoding the antisense oligonucleotides at a variety of concentrations. Other incubation conditions known to those in art (e.g., temperature or cell concentration) can also be varied. Inhibition of HID-5 expression can be tested by methods known to those in the art, e.g., methods such as those disclosed herein. However, the methods of the invention will preferably be in vivo.

As used herein, "prophylaxis" can mean complete prevention of the symptoms of a disease (e.g., breast cancer such DCIS), a delay in onset of the symptoms of a disease, or a lessening in the severity of subsequently developed disease symptoms. "Prevention" should mean that symptoms of the disease (e.g., breast cancer) are essentially absent. As used herein, "therapy" can mean a complete abolishment of the symptoms of a disease or a decrease in the severity of the symptoms of the disease. As used herein, a "protective" regimen is a regimen that is prophylactic and/or therapeutic.

The antisense methods are generally useful for cancer cell (e.g., breast cancer cell) proliferation-inhibiting and/or survival-inhibiting therapy or prophylaxis. They can be administered to mammalian subjects (e.g., human breast cancer patients) alone or in conjunction with other drugs and/or radiotherapy.

Where antisense oligonucleotides per se are administered, they can be suspended in a pharmaceutically-acceptable carrier (e.g., physiological saline) and administered orally, intrarectally, intravaginally, intranasally, intragastrically, intratracheally, or intrapulmonarily, or injected subcutaneously, intramuscularly, intrathecally, intraperitoneally, intravenously. They can also be delivered directly to tumor cells, e.g., to a tumor or a tumor bed following surgical excision of the tumor, in order to kill any remaining tumor cells. The dosage required depends on the choice of the route of administration; the nature of the formulation; the nature of the patient's illness; the subject's size, weight, surface area, age, and sex; other drugs being administered; and the judgment of the attending physician. Suitable dosages are generally in the range of 0.01 mg/kg-100 mg/kg. Wide variations in the needed dosage are to be expected in view of the variety of compounds available and the differing efficiencies of various routes of administration. For example, oral administration would be expected to require higher dosages than administration by intravenous injection. Variations in these dosage levels can be adjusted using standard empirical routines for optimization as is well understood in the art. Administrations can be single or multiple (e.g., 2-, 3-, 4-, 6-, 8-, 10-, 20-, 50-, 100-, 150-, or more fold). Encapsulation of the polypeptide in a suitable delivery vehicle (e.g., polymeric microparticles or implantable devices) may increase the efficiency of delivery, particularly for oral delivery.

Where an expression vector containing a nucleic sequence (operably linked to a TRE) encoding the antisense oligonucleotide is administered to a subject, expression of the coding sequence can be directed to any cell in the body of the subject. However, expression will preferably be directed to cells in the vicinity of the tumor cells whose proliferation and/or survival it is desired to inhibit. Expression of the coding sequence can be directed to the tumor cells themselves. This can be achieved by, for example, the use of polymeric, biodegradable microparticle or microcapsule delivery devices known in the art.

Another way to achieve uptake of the nucleic acid is using liposomes, prepared by standard methods. The vectors can be incorporated alone into these delivery vehicles or co-incorporated with tissue-specific or tumor-specific antibodies. Alternatively, one can prepare a molecular conjugate composed of a plasmid or other vector attached to poly-L-lysine by electrostatic or covalent forces. Poly-L-lysine binds to a ligand that can bind to a receptor on target cells [Cristiano et al. (1995), J. Mol. Med. 73:479]. Alternatively, tissue-specific targeting can be achieved by the use of tissue-specific transcriptional/translational regulatory elements (TRE), e.g., promoters and enhancers, which are known in the art. Delivery of "naked DNA" (i.e., without a delivery vehicle) to an intramuscular, intradermal, or subcutaneous site is another means to achieve in vivo expression.

Enhancers provide expression specificity in terms of time, location, and level. Unlike a promoter, an enhancer can function when located at variable distances from the transcription initiation site, provided a promoter is present. An enhancer can also be located downstream of the transcription initiation site. To bring a coding sequence under the control of a promoter, it is necessary to position the translation initiation site of the translational reading frame of the peptide or polypeptide between one and about fifty nucleotides downstream (3') of the promoter. The coding sequence of the expression vector is operatively linked to a transcription terminating region.

The transcriptional/translational regulatory elements referred to above include, but are not limited to, inducible and non-inducible promoters, enhancers, operators and other elements that are known to those skilled in the art and that drive or otherwise regulate gene expression. Such regulatory elements include but are not limited to the cytomegalovirus hCMV immediate early gene, the early or late promoters of SV40 adenovirus, the lac system, the trp system, the TAC system, the TRC system, the major operator and promoter regions of phage A, the control regions of fd coat protein, the promoter for 3-phosphoglycerate kinase, the promoters of acid phosphatase, and the promoters of the yeast α-mating factors.

Suitable expression vectors include plasmids and viral vectors such as herpes viruses, retroviruses, vaccinia viruses, attenuated vaccinia viruses, canary pox viruses, adenoviruses and adeno-associated viruses, among others.

Polynucleotides can be administered in a pharmaceutically acceptable carrier. Pharmaceutically acceptable carriers are biologically compatible vehicles that are suitable for administration to a human, e.g., physiological saline or liposomes. A therapeutically effective amount is an amount of the polynucleotide that is capable of producing a medically desirable result (e.g., decreased proliferation and or survival of cancer cells) in a treated animal. As is well known in the medical arts, the dosage for any one patient depends upon many factors, including the patient's size, body surface area, age, the particular compound to be administered, sex, time and route of administration, general health, and other drugs being administered concurrently. Dosages will vary, but a preferred dosage for administration of polynucleotide is from approximately $10^6$ to approximately $10^{12}$ copies of the polynucleotide molecule. This dose can be repeatedly administered, as needed. Routes of administration can be any of those listed above.

Double-stranded interfering RNA (RNAi) homologous to HID-5 DNA can also be used to reduce expression of HID-5 in a cell. See, e.g., Fire et al. (1998) Nature 391:806-811; Romano and Masino (1992) Mol. Microbiol. 6:3343-3353; Cogoni et al. (1996) EMBO J. 15:3153-3163; Cogoni and Masino (1999) Nature 399:166-169; Misquitta and Paterson (1999) Proc. Natl. Acad. Sci. USA 96:1451-1456; and Kennerdell and Carthew (1998) Cell 95:1017-1026.

The sense and anti-sense RNA strands of RNAi can be individually constructed using chemical synthesis and enzymatic ligation reactions using procedures known in the art. For example, each strand can be chemically synthesized using naturally occurring nucleotides or variously modified nucleotides designed to increase the biological stability of the molecule or to increase the physical stability of the duplex formed between the sense and anti-sense strands, e.g., phosphorothioate derivatives and acridine substituted nucleotides. The sense or anti-sense strand can also be produced biologically using an expression vector into which a target HID-5 sequence (full-length or a fragment) has been subcloned in a sense or anti-sense orientation. The sense and anti-sense RNA strands can be annealed in vitro before delivery of the dsRNA to any of cancer cells disclosed herein. Alternatively, annealing can occur in vivo after the sense and anti-sense strands are sequentially delivered to the cancer cells.

Double-stranded RNA interference can also be achieved by introducing into cancer cells a polyiucleotide from which sense and anti-sense RNAs can be transcribed under the direction of separate promoters, or a single RNA molecule containing both sense and anti-sense sequences can be transcribed under the direction of a single promoter.

One of skill in the art will appreciate that RNAi methods can be, as for the antisense methods described above, in vitro and in vivo. Moreover, methods and conditions of delivery and the species to which the RNAi methods can be applied are the same as those for antisense oligonucleotides.

The antisense and RNAi methods of the invention can be applied to a wide range of species, e.g., humans, non-human primates, horses, cattle, pigs, sheep, goats, dogs, cats, rabbits, guinea pigs, hamsters, rats, and mice.

The SAGE analysis described in Example 2 showed that expression of calgranulin B/S100A9 and connexin 43, in addition to HID-5/psoriason, was upregulated in high grade DCIS cells relative to normal breast epithelial cells and intermediate grade DCIS cells. Thus the invention also features methods of inhibiting calgranulin B/S100A9 and/or connexin 43 expression in cells for the same purposes described above for inhibiting expression of HID-5. Relevant methods are obvious adaptions of those described above for inhibition of HID-5 expression in high grade breast cancers.

Passive Immunoprotection

As used herein, "passive immunoprotection" means administration of one or more HID-5-binding agents to a subject that has, is suspected of having, or is at risk of having a high grade breast cancer, e.g., high grade DCIS. Thus, passive immunoprotection can be prophylactic and/or therapeutic. As used herein, "HID-5-binding agents" are agents that bind to HID-5 and thereby inhibit the ability of HID-5 to enhance proliferation and/or survival of cells such as high grade breast cancer cells, e.g., high grade DCIS cells. It is understood that the term "inhibit" includes "completely inhibit" and "partially inhibit." A HID-5 binding agent useful for the invention has the capacity to inhibit the ability of HID-5 to enhance the proliferation and/or survival of the cells by at least 20% (e.g., at least: 20%; 30%; 40%; 50%; 60%; 70%; 80%; 90%; 95%; 98%; 99%; 99.5%, or even 100%). HID-5-binding agents can be, for example, a soluble (i.e., not cell-bound) form of a HID-5 receptor or an antibody specific for HID-5.

Antibodies can be polyclonal or monoclonal antibodies; methods for producing both types of antibody are known in the art. The antibodies can be of any class (e.g., IgM, IgG, IgA, IgD, or IgE) and be generated in any of the species recited herein. They are preferably IgG antibodies. Recombinant antibodies specific for HID-5, such as chimeric and humanized monoclonal antibodies comprising both human and non-human portions, can also be used in the methods of the invention. Such chimeric and humanized monoclonal antibodies can be produced by recombinant DNA techniques known in the art, for example, using methods described in Robinson et al., International Patent Publication PCT/US86/02269; Akira et al., European Patent Application 184,187; Taniguchi, European Patent Application 171,496; Morrison et al., European Patent Application 173,494; Neuberger et al., PCT Application WO86/01533; Cabilly et al., U.S. Pat. No. 4,816,567; Cabilly et al., European Patent Application 125, 023; Better et al. (1988) Science 240, 1041-43; Liu et al. (1987) J. Immunol. 139, 3521-26; Sun et al. (1987) PNAS 84, 214-18; Nishimura et al. (1987) Canc. Res. 47, 999-1005; Wood et al. (1985) Nature 314, 446-49; Shaw et al. (1988) J. Natl. Cancer Inst. 80, 1553-59; Morrison, (1985) Science 229, 1202-07; Oi et al. (1986) BioTechniques 4, 214; Winter, U.S. Pat. No. 5,225,539; Jones et al. (1986) Nature 321, 552-25; Veroeyan et al. (1988) Science 239, 1534; and Beidler et al. (1988) J. Immunol. 141, 4053-60.

Also useful for the invention are antibody fragments and derivatives that contain at least the functional portion of the antigen-binding domain of an antibody that binds to HID-5. Antibody fragments that contain the binding domain of the molecule can be generated by known techniques. Such fragments include, but are not limited to: $F(ab')_2$ fragments that can be produced by pepsin digestion of antibody molecules; Fab fragments that can be generated by reducing the disulfide bridges of $F(ab')_2$ fragments; and Fab fragments that can be generated by treating antibody molecules with papain and a reducing agent. See, e.g., National Institutes of Health, 1 Current Protocols In Immunology, Coligan et al., ed. 2.8, 2.10 (Wiley Interscience, 1991). Antibody fragments also include Fv fragments, i.e., antibody products in which there are few or no constant region amino acid residues. A single chain Fv fragment (scFv) is a single polypeptide chain that includes both the heavy and light chain variable regions of the antibody from which the scFv is derived. Such fragments can be produced, for example, as described in U.S. Pat. No. 4,642,334, which is incorporated herein by reference in its entirety. For a human subject, the antibody can be a "humanized" version of a monoclonal antibody originally generated in a different species.

HID-5-binding agents can be administered to any of the species listed herein. The HID-5-binding agents will preferably, but not necessarily, be of the same species as the subject to which they are administered. A single polyclonal or monoclonal antibody can be administered, or two or more (e.g., two, three, four, five, six, seven, eight, nine, ten, 12, 14, 16, 18, or 20) polyclonal antibodies or monoclonal antibodies can be given. The HID-5-binding agents can be administered to subjects prior to, subsequently to, or at the same time as the HID-5-expression inhibitors (see above).

The dosage of HID-5-binding agents required depends on the route of administration, the nature of the formulation, the nature of the patient's illness, the subject's size, weight, surface area, age, and sex, other drugs being administered, and the judgment of the attending physician. Suitable dosages are in the range of 0.01-100.0 mg/kg. The HID-5-binding agents can be administered by any of the routes disclosed herein, but will generally be administered intravenously, intramuscularly, or subcutaneously. Wide variations in the needed dosage are to be expected in view of the variety of HID-5-binding agents (e.g., HID-5-specific antibodies) available and the differing efficiencies of various routes of administration. Variations in these dosage levels can be adjusted using standard empirical routines for optimization, as is well understood in the art. Administrations can be single or multiple (e.g., 2- or 3-, 4-, 6-, 8-, 10-, 20-, 50-, 100-, 150-, or more fold).

Methods to test whether a compound or antibody is therapeutic for, or prophylactic against, a particular disease are known in the art. Where a therapeutic effect is being tested, a test population displaying symptoms of the disease (e.g., breast cancer such as DCIS) is treated with a HID-5 expression inhibitor or HID-5-binding agent using any of the above-described strategies. A control population, also displaying symptoms of the disease, is treated, using the same methodology, with a placebo. Disappearance or a decrease of the disease symptoms in the test subjects would indicate that the compound or antibody was an effective therapeutic agent. By applying the same strategies to subjects at risk of having the disease, the compounds and antibodies can be tested for efficacy as prophylactic agents. In this situation, prevention of or delay in onset of disease symptoms is tested.

The invention is illustrated, not limited, by the following examples.

EXAMPLES

Example 1

Materials and Methods

Cell Lines and Culture Conditions

The MDA-MB468 and MCF10A cell lines were obtained from American Type Culture Collection (ATCC; Manassas, Va.) and were maintained in McCoy's medium (Life Technologies, Gaithersburg, Md.) containing 10% fetal bovine serum (FBS) and in DMEM/F12 medium (Life Technologies) containing 5% horse serum and supplemented with 20 ng/ml epidermal growth factor, 100 ng/ml cholera toxin, 0.01 mg/ml insulin, and 500 ng/ml hydrocortisone, respectively. To determine the effect of serum deprivation on HID-5/psoriasin expression in subconfluent or confluent cultures, MCF10A cells were switched to 0.2% serum containing DMEM/F12 medium and incubated for the indicated time. The effect of confluency was analyzed by maintaining MCF10A cells under confluent conditions for the indicated time with frequent (every other day) medium changes. For suspension cultures, MCF10A cells were trypsinized, resuspended in fresh medium ($1.75 \times 10^5$ cells/ml medium), plated into poly-2-hydroxy-ethylmethacrylate (Aldrich, St. Louis, Mo.) coated (1 mg/cm$^2$ in 100% ethanol) petri dishes, and incubated for the indicated time.

Generation of Polyclonal and Monoclonal Anti-HID-5/psoriasin Antibodies

A rabbit polyclonal anti-HID-5 antibody was generated by immunization with a synthetic peptide corresponding to amino acids 83-100 of human HID-5 (TDYHKQSHGAAPC-SGGSQ) (SEQ ID NO:3). In FIG. 4A is shown the amino acid sequence (SEQ ID NO:1) of full length, human HID-5 and in FIG. 4B is shown the nucleotide sequence (SEQ ID NO:2) of cDNA encoding full-length human mature HID-5. For the generation of mouse monoclonal antibodies, a PCR-generated BamHI-HindIII cDNA fragment encoding full-length human HID-5 was subcloned into BamHI-HindIII sites of pQE-30 (Qiagen Sciences, Germantown, Md.) yielding a construct that encodes HID-5 with an N-terminal hexahistidine sequence. The protein was expressed in M15[pREP4] bacteria, purified to homogeneity using denaturing urea buffer and NiNTA beads (Qiagen Sciences). Bound protein was eluted in 50 mM Tris pH 7.5, 500 mM imidazole, 100 mM EDTA, 1 M NaCl, 10% glycerol, 1 mM DTT. In collaboration with Imgenex, San Diego, Calif., the protein was used to hyperimmunize BALB/c mice, which provided a source of antibody producing cells for generating HID-5-specific-monoclonal antibodies. The resulting anti-HID-5 monoclonal antibodies are commercially available from Imgenex.

Western Blot Analysis, Immunohistochemistry, and Tissue Microarrays

Western blot analyses of cell lysates and immunohistochemistry were performed using anti-CD45 panleukocyte (Dako, Glostrup, Denmark), anti-estrogen receptor α (ERα), anti-erbB2, and anti-HID-5 (clone 1068-1; designated "Cl 1" in the right panel of FIG. 2A) antibodies as previously described [Krop et al., (2001) Proc. Natl. Acad. Sci. U.S.A. 98:9796-9801; Leach et al. (1998) Cancer Res. 56:235-240]. Tissue microarrays were purchased from Imgenex or were generated as previously described [Kononen et al. (1998) Nat. Med. 4:844-847].

Fluorescence in Situ Hybridization (FISH), Real-time PCR, Northern Blots and mRNA in Situ Hybridization FISH analysis of metaphase chromosome preparations from peripheral blood lymphocytes obtained from normal human males was performed according to a previously described method [Ney et al. (1993) Mol. Cell. Biol. 13:5604-5612]. Interphase nuclei from disaggregated formalin fixed, paraffin embedded tumor tissue were prepared and FISH was performed according to previously described methods [Kuchinka et al. (19950 Mod. Pathol. 8:183-186]. Metaphase chromosomes and interphase nuclei were counterstained with 4,6-diamidino-2-phenylindole-dihydrochloride (DAPI). Laser capture microdissection, real-time PCR analysis, RNA isolation, and Northern blot analysis were performed as previously described [Krop et al. (2001) Proc. Natl. Acad. Sci. U.S.A. 98:9796-9801]. mRNA in situ hybridizations using $^{33}$P-labeled sense (control) or anti-sense HID-5 ribo-probes were performed as previously described [Rosen et al. (1999) Mol. Cell. 4:611-617].

Example 2

Genes Aberrantly Expressed in DCIS and Psoriatic Lesions

The generation of SAGE libraries has been previously described [e.g., Porter et al. (2001) Cancer Res. 61:5697-5702]. Comparison of SAGE libraries generated from two normal breast epithelial samples ("Normal 1" and "Normal 2"), estrogen receptor (ER)-expressing, intermediate grade DCIS cells ("IM DCIS (ER+)") and ER-non-expressing, high grade DCIS ("HG DCIS (ER)") revealed that HID-5 is among the most highly differentially expressed transcripts and is one of the most abundant mRNAs in high grade DCIS (Table 1).

In addition to mRNA transcribed from the gene encoding psoriasin mRNA, S100A9, another S100 protein, was also highly expressed in high grade DCIS (Table 1). Both genes are located on the long (q) arm of chromosome 1 and the expression of both is up-regulated in psoriatic keratinocytes.

TABLE 1

Genes aberrantly expressed in psoriatic keratinocytes and high-grade DCIS

| SAGE tag | SEQ ID NO: | Gene | Unigene ID | Number of SAGE tags detected | | | |
|---|---|---|---|---|---|---|---|
| | | | | Normal 1 | Normal 2 | HG DCIS (ER−) | IM DCIS (ER+) |
| GAGCAGCGCC | 4 | Psoriasin/S100A7 | 112408 | 10 | 0 | 568 | 1 |
| GTGGCCACGG | 5 | Calgranulin B/S100A9 | 112405 | 16 | 16 | 111 | 0 |
| TGTTCTGGAG | 6 | Connexin 43 | 74471 | 1 | 2 | 28 | 1 |
| TGGAAGCACT | 7 | Interleukin 8 | 624 | 205 | 196 | 4 | 21 |
| CGAATGTCCT | 8 | Keratin 6 | 91539 | 29 | 27 | 0 | 0 |
| CTATAGCATA | 9 | Amphiregulin | 1257 | 16 | 13 | 0 | 1 |
| GGCACCTCAG | 10 | Interleukin 6 | 93913 | 17 | 2 | 0 | 0 |
| GTGGCCCACG | 11 | Interleukin 6 receptor | 193400 | 5 | 3 | 0 | 0 |
| CCTGTAATCC | 12 | SCCA1 | 227948 | 0 | 0 | 3 | 0 |

SCCA1-Squamous Cell Carcinoma Antigen-1

The chromosomal localization of other highly differentially expressed genes and the expression level of genes implicated in psoriatic lesions was examined (Table 1). Surprisingly, a significant fraction (13 out of 46 reliably mapped genes) of genes specifically overexpressed in high grade DCIS is located on the long arm of chromosome 1 (Table 1). Structural abnormalities of chromosome 1 are among the most frequent cytogenetic abnormalities in breast carcinomas and several genes involved in epidermal differentiation map to chromosome 1 q [Volz et al. (1993) Genomics 18:92-99; Tirkkonen et al. (1998) Genes Clirom. Cancer 21:177-184].

To determine if the overexpression of these 13 genes in high grade DCIS is due to aneuploidy/aneusomy of chromosome 1 q, FISH analysis was carried out using as probes two non-overlapping BACs (bacterial artificial chromosomes) containing the psoriasin and the ephrin A4 genes, respectively. The analysis was performed on metaphase spreads from a normal individual and interphase nuclei from the DCIS used for SAGE (data not shown). Following the confirmation of the chromosomal assignment of the HID-5/psoriasin gene to the long arm of chromosome 1 in band q21 by metaphase spread analysis, interphase nuclei from the DCIS tumor tissue were hybridized with the BAC containing the gene (data not shown). Two hybridization signals were noted in 31/33 (94%) nuclei examined, consistent with a normal number of copies for the genomic region tested. This result indicated that the aberrant expression of psoriasin/HID-5 in high grade DCIS lesion is not caused by amplification of the psoriasin/HID-5 locus.

In addition to psoriasin, several other genes known to be up-regulated in psoriatic keratinocytes were aberrantly expressed in high grade DCIS (Table 1) [Celis et al. (1990) Electrophoresis 11:242-254; Labarthe et al. (1998) J. Invest. Dermatol. 111:72-76; Rivas et al. (1997) J. Invest. Dermatol. 108:188-194). These genes included those encoding S100A9, connexin 43, interleukins 6 and 8, interleukin 6 receptor, amphiregulin, and keratin 6. SCCA1 (squamous cell carcinoma antigen 1) mRNA expression was also slightly up-regulated in high grade DCIS although, due to the low abundance of this mRNA, the detected difference did not reach statistical significance. The aberrant expression of these genes in high grade DCIS and psoriatic keratinocytes could be due to hyperproliferation, abnormal differentiation, or lymphocytic infiltration characteristic of both types of lesions [Bos et al. (1999) Immunol. Today 20:40-46; Page et al. (2000) Curr. Opin. Oncol. 12:526-531].

Example 3

HID-5/Psoriasin Expression in Mammary Epithelial Cells in vivo and in vitro

To evaluate the expression of HID-5/psoriasin in primary breast carcinomas, real-time PCR analysis of 11 LCM (Laser Capture Microdissection) purified primary tumors and corresponding normal mammary epithelium samples (FIG. 1A). Thus each tumor sample from a patient was compared to normal mammary epithelium from the same patient. In all cases, except for an in situ, ER-expressing, progesterone receptor-expressing low grade lesion (sample 57) and an invasive, ER-expressing, progesterone receptor expressing, intermediate grade lesion (sample 65), HID-5/psoriasin mRNA levels were significantly ($\geqq 10$ fold) increased relative to corresponding normal mammary epithelium (FIG. 1A).

Figure 1B:
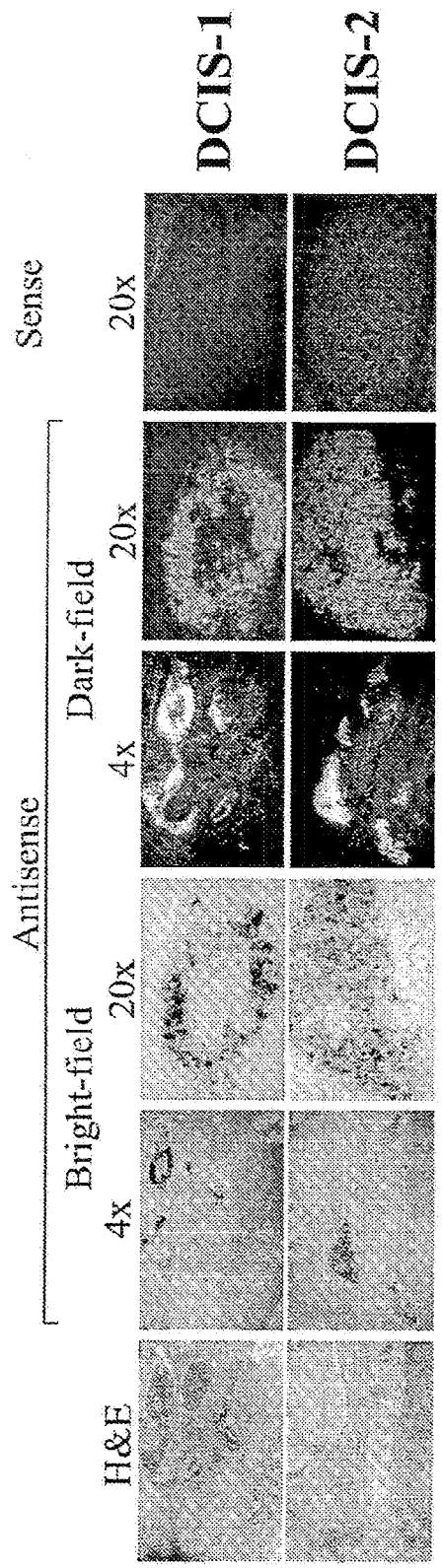
FIG. 1B is a series of photomicrographs of histological sections of two high grade comedo DCIS tumors ("DCIS-1" and "DCIS-2") that were stained with hemotoxylin and eosin ("H&E") or subjected to in situ hybridization analysis with $^{33}$P-labeled antisense or sense HID-5/psoriasin riboprobes. The samples analyzed with the antisense riboprobe were photographed under "Bright-field" and "Dark-field" conditions using objective lens magnifications of 4× and 20×. The samples analyzed with the sense riboprobe were photographed under "Dark-field" conditions only using an objective lens magnification of 20×. Similar in situ hybridization analyses of two low and two intermediate grade DCIS tumors failed to detect HID-5/psoriasin mRNA in any of the samples.

To confirm HID-5/psoriasin expression in high grade DCIS epithelial cells at the cellular level, a mRNA in situ hybridization analysis of two low, two intermediate, and two high grade DCIS tumors and corresponding normal epithelium was performed (FIG. 1B and data not shown). HID-5/psoriasin is highly and specifically expressed by the tumor cells of the two high grade comedo DCIS (FIG. 1B). In contrast, no hybridization signal was detected in low and intermediate grade DCIS and normal mammary epithelial cells (FIG. 1B and data not shown).

To analyze the expression of HID-5/psoriasin protein, polyclonal and monoclonal antibodies specific for human HID-5/psoriasin were generated and characterized. Both the polyclonal antibody and the monoclonal antibodies bound to recombinant and the endogenous HID-5/psoriasin proteins migrating as a ~11 kDa single band in sodium dodecyl sulfate polyacrylamide gel electrophoresis (SDS-PAGE) (FIG. 2A). A series of experiments were performed to test whether HID-5/psoriasin expression can be detected under various growth conditions in MCF10A cells. MCF10A cells are normal immortalized human mammary epithelial cells that demonstrate no (or a very low level of) HID-5/psoriasin expression in sparse, exponentially growing cultures. In order to mimic the conditions likely to occur in vivo in high grade DCIS and psoriatic skin lesions, the MCF10A cells were cultured in medium serum containing a low concentration of serum (0.2% versus high (5%)) and under confluent (versus sparse) conditions. Culture of the cells in a low concentration of serum and under confluent conditions (regardless of the serum concentration) led to dramatic up-regulation of HID-5/psoriasin protein levels (FIG. 2B). The highest HID-5/psoriasin protein levels were observed in confluent, serum deprived cells (FIG. 2B).

The effect of cell detachment from extracellular matrix was tested by culturing MCF10A cells in suspension for several days. Lack of cell anchorage also dramatically increased HID-5/psoriasin protein levels (FIG. 2C). Northern blot analysis indicated that the up-regulation of HID-5/psoriasin expression by cell suspension and confluency occurred at the mRNA level (FIG. 2D). Cell cycle analysis of MCF10A cells revealed that serum deprivation, confluency and lack of cell anchorage ultimately results in G1 arrest followed by apoptosis (data not shown). The dramatic up-regulation of HID-5/psoriasin expression by these extracellular signals indicates that HID-5/psoriasin may play a role in the regulation of these cellular processes. Interestingly, keratinocytes derived from psoriatic lesions have been shown to be resistant to apoptosis compared to those derived from normal skin [Wrone-Smith et al. (1997) Am J. Pathol. 151:1321-1329]. High grade DCIS tumors demonstrate high apoptotic rates [Page et al. (2000) Curr. Opin. Oncol. 12:526-531] and surviving tumor cells are likely to be relatively resistant to apoptosis.

Example 4

HID-5/Psoriasin is a Partially Secreted Cytoplasmic Protein

Figure 3A:
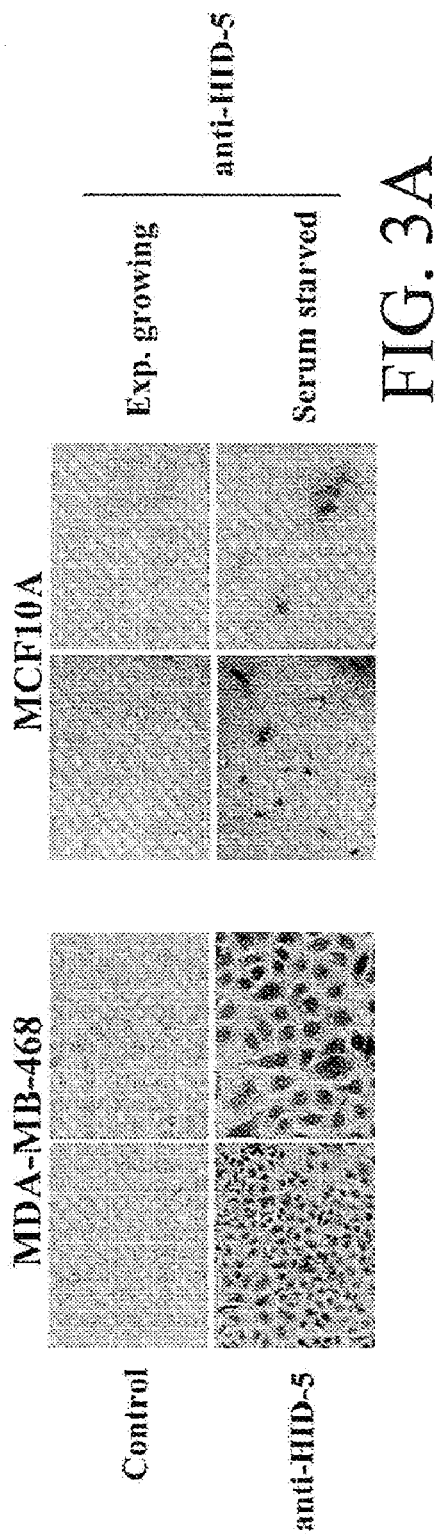
FIG. 3A is a series of photomicrographs of cultures of MDA-MB-468 breast cancer cells (left panel) and MCF10A normal breast epithelial cells growing exponentially ("Exp. growing") or in the absence of serum ("Serum starved") (right panel). The MDA-MB-468 cells were stained with either an anti-HID-5 monoclonal antibody (left panel, bottom photomicrographs) or control normal mouse serum (left panel, top photomicrographs). The MCF10A cells were stained with an anti-HID-5 monoclonal antibody. No staining was seen in MCF10A cells stained with control normal mouse serum. The left photomicrographs were taken at an objective lens magnification of 2× and the right photomicrographs at an objective lens magnification of 10×.
Figure 3B:
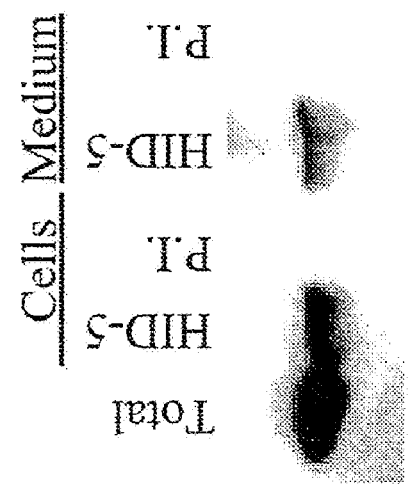
FIG. 3B is a photograph of an immunoblot showing intracellular localization and secretion of HID-5 by MDA-MB-468 cells in culture. Total MDA-MB-468 cell lysate ("Total") and proteins immunoprecipitated from lysates ("Cells") or culture supernatant ("Medium") of MDA-MB-468 cells by a polyclonal anti-HID-5 antibody ("HID-5") or control pre-immune serum ("P.I.") were resolved by SDS-PAGE and subjected to immunoblot analysis. The position of HID-5 ("HID-5/Psoriasin") on the immunoblot is shown.

To determine the subcellular localization of the HID-5/psoriasin protein, immunohistochemistry on MDA-MB468 breast cancer cells and exponentially growing and serum starved MCF10A cells was performed using the monoclonal anti-HID-5/psoriasin antibody designated "Cl 1" in FIG. 2A (FIG. 3A). Both nuclear and cytoplasmic staining were detected in MDA-MB468 cells and in serum-starved MCF10A cells, whereas no staining was seen using a negative control antiserum or in exponentially growing MCF10A cells (FIG. 3A). Previous results demonstrated that psoriasin can be detected in the urine of bladder cancer patients and is partially secreted by psoriatic keratinocytes even though it contains no signal peptide [Madsen et al. (1991) J. Invest. Dermatol. 97:701-712; Ostergaard et al. (1999) Electrophoresis 20:349-354]. To determine if HID-5/psoriasin is also secreted by breast cancer cells, immunoprecipitations were performed on cell lysate and culture medium of MDA-MB468 cells using an anti-HID-5/psoriasin polyclonal antibody. Immunoprecipitates were resolved by SDS-PAGE and analyzed by western blotting with a polyclonal anti-HID-5 antibody. HID-5/psoriasin protein was precipitated from both cell lysate and the culture medium with the anti-HID-5 antibody ("HID-5"), whereas no protein was precipitated by control pre-immune serum ("P.I.") (FIG. 3B). Thus, HID-5/psoriasin protein is partially secreted or released by breast cancer cells. It is thus likely that it is detectable in the body fluids (e.g., blood and urine) of breast cancer patients. Detection of HID-5 in such body fluids can therefore be a test for high grade breast cancer, e.g., high grade DCIS.

Example 5

Figure 3C:
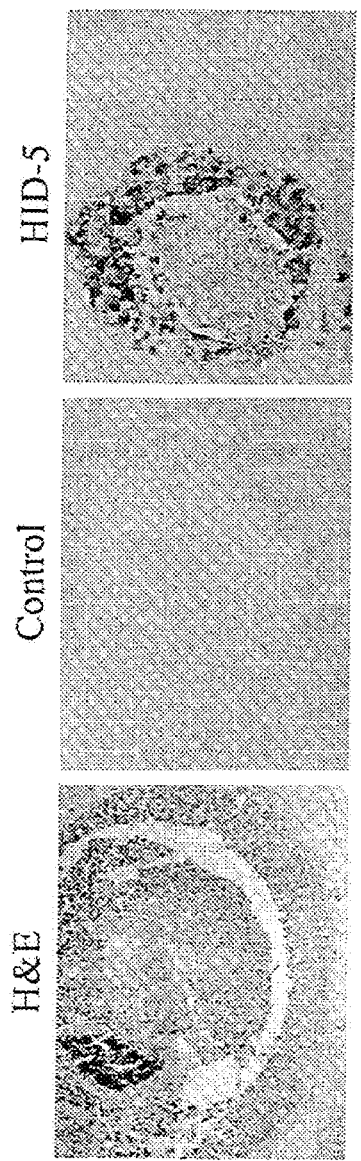
FIG. 3C is a series of three photomicrographs of sections of a high grade comedo DCIS lesion that were stained with hemotoxylin and eosin ("H&E") (left photograph), anti-HID-5 monoclonal antibody ("HID-5") (right photograph), and control normal mouse serum ("Control") (middle photograph).

Immunohistohemical Analysis of HID-5/Psoriasin Protein Levels in Primary Breast Carcinomas To analyze the in vivo expression of the HID-5/psoriasin protein, immunohistochemical analysis of formalin-fixed, paraffin-embedded breast carcinomas was performed using monoclonal anti-HID-5/psoriasin antibodies. To assess the reliability of the staining, a high grade comedo DCIS tumor previously shown by mRNA in situ hybridization to express HID-5/psoriasin was analyzed. Intense immunohistochemical staining was detected in the tumor cells using anti-HID-5 antibody ("HID-5"), while no staining was seen using isotype control serum ("Control") (FIG. 3C).

Figure 3D:
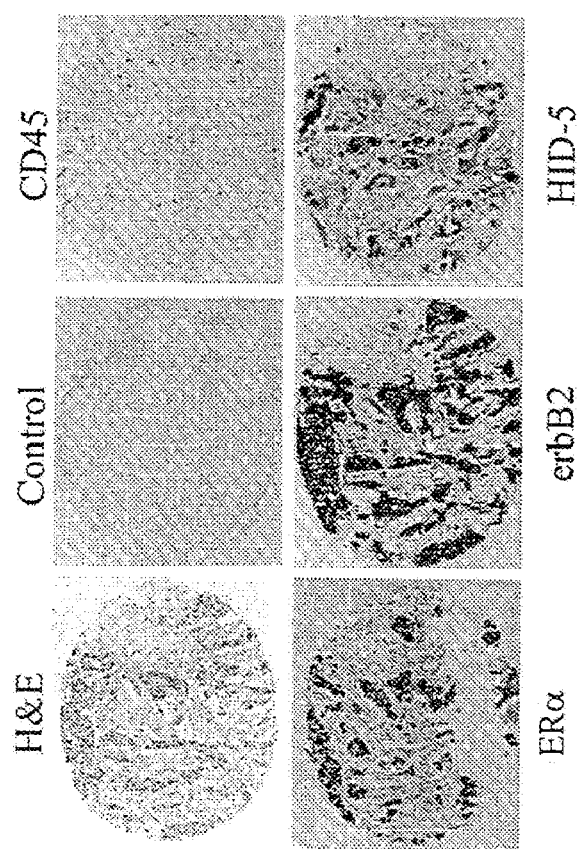
FIG. 3D is a series of six photomicrographs of samples from a representative breast tumor in a tissue array stained with hemotoxylin and eosin ("H&E"), monoclonal antibodies specific for HID-5, ERα, erbB2, or CD45, or control normal mouse serum ("Control").
Figure 3E:
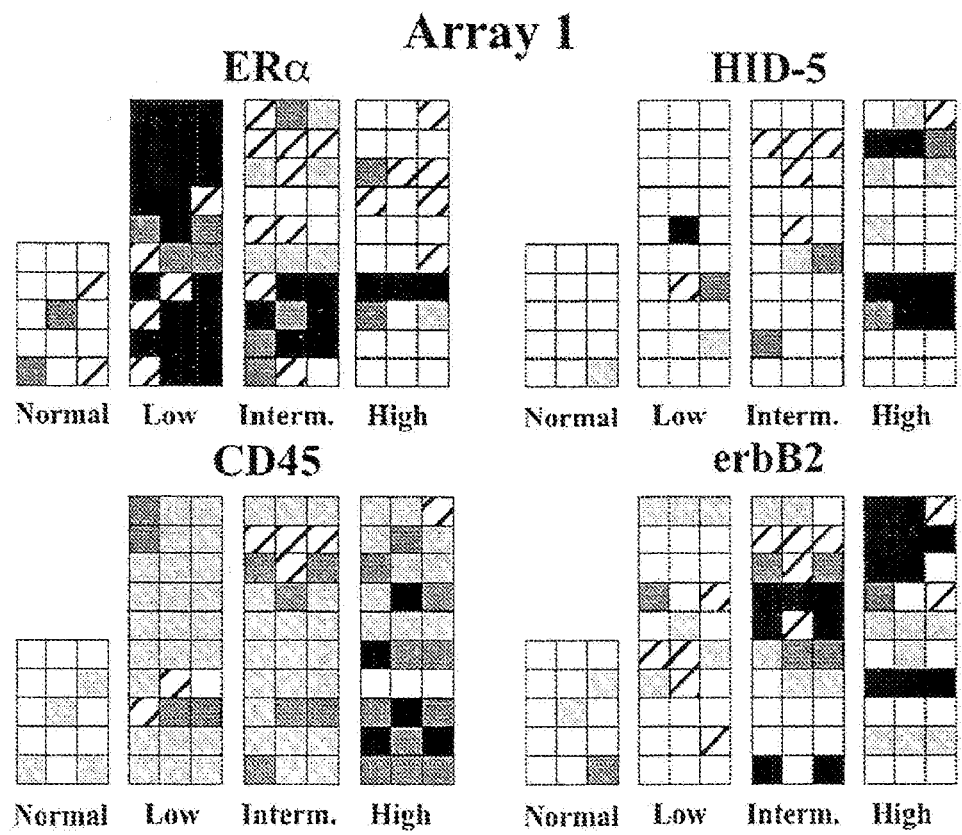
FIG. 3E is a schematic representation summarizing the results of immunochemical analyses of two tissue arrays. Array 1 was composed of five individual samples of normal breast tissue and 30 individual samples of primary invasive breast carcinomas (ten each of low, intermediate, and high grade) and array 2 was composed of six individual samples of normal breast tissue, three samples of benign hyperproliferative lesions and 49 samples of primary invasive ductal carcinomas. In array 1, three punches (in horizontal rows) of each tumor sample were affixed to the slide and tumors were grouped according to their histologic grade (low, intermediate, and high grade tumors). Array 1 tumor samples were analyzed for expression of HID-5, ER α (ERα), and erbB2 and for the presence of leukocytes using an antibody specific for CD45, a panleukocyte antigen. In array 2, the first vertical row contained the six samples of normal breast tissue, three samples of benign hyperproliferative lesions, and an empty spot (indicated by the hatched square). Array 2 samples were analyzed for expression of ERα, progesterone receptor (PR), and p53; data from the analysis of HID-5 and ERα expression are shown. Intensity of staining is indicated by the intensity of shading, with white representing no detectable staining and black being very intense staining. Hatched rectangles represent either empty spots on the arrays or samples lost during the staining procedure.
Figure 3E:
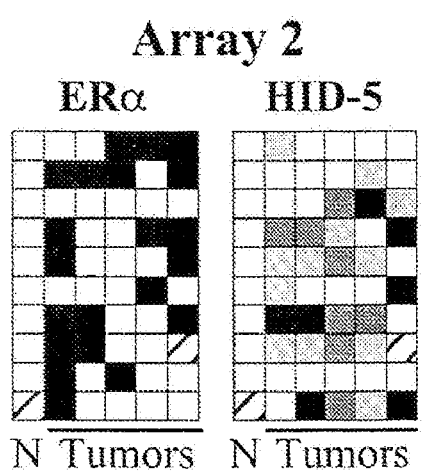

Two tissue microarrays were examined. Array 1 was composed of five individual samples of normal breast tissue and 30 individual samples of primary invasive breast carcinomas (ten each of low, intermediate, and high grade) and array 2 was composed of six individual samples of normal breast tissue, three samples of benign hyperproliferative lesions and 49 samples of primary invasive ductal carcinomas. Diagrammatic representations of the two arrays are shown in FIG. 3E. In array 1, three punches (in horizontal rows) of each tumor sample were affixed to the slide and tumors were grouped according to their histologic grade (low, ntermediate, and high grade tumors). Array 1 tumor samples were also analyzed for expression of ER α (ERα) and erbB2 and for the presence of leukocytes using an antibody specific for CD45, a panleukocyte antigen. In array 2, the first vertical row contained the six samples of normal breast tissue, the three samples of benign hyperproliferative lesions, and an empty spot (indicated by the hatched square). Array 2 samples were analyzed for expression of ERα, progesterone receptor (PR), and p53. Staining from a representative tumor is shown in FIG. 3D and the results are summarized in FIG. 3E.

As expected, low grade tumors were mostly ERα positive, erbB2 negative and CD45 low, while high grade ones were mostly ERα negative, erbB2 positive, and CD45 high. No significant HID-5/psoriasin expression was detected in any of the normal breast tissue samples nor in the benign hyperproliferative lesions (FIG. 3E). HID-5/psoriasin positive invasive tumors were mostly ERα negative. Among the 78 tumors examined, 38 were HID-5/psoriasin positive (15 ERα+ and 23 ERα−) and 40 were HID-5/psoriasin negative (26 ERα+ and 14 ERα−). Based on these results HID-5/psoriasin positive tumors are more likely to be ERα negative (P=0.04, Fisher exact test). In one of three punches from a low grade tumor, a high level of HID-5/psoriasin was observed (FIG. 3E, Array 1); however, this tumor was later found to be a high grade DCIS lesion.

HID-5/psoriasin is a putative chemoattractant for lymphocytes, and both psoriatic skin and high grade DCIS lesions are frequently unfiltrated by lymphocytes [Bos et al. (1999) Immunol. Today 20:40-46; Page et al. (2000) Curr. Opin. Oncol. 12:526-531]. Although lymphocytic infiltration, as indicated by CD45 staining, was frequent in high-grade tumors, no clear association was seen between CD45 and HID-5/psoriasin positivity (FIG. 3E). This could be due to the relatively small sample size or to the fact that the carcinoma were invasive and not in situ.

To determine if the expression of HID-5/psoriasin correlates with histopathologic or clinical characteristics of breast tumors, a separate immunohistochemical analysis of 722 breast tumors was performed. Overall, approximately 30% of the tumors were HID-5/psoriasin positive. Statistical analysis of the immunohistochemistry data showed that expression of HID-5/psoriasin was statistically significantly different in in situ and primary invasive tumors, and distant metastasis. Specifically, in situ and primary invasive tumors were more likely to be HID5/psoriasin positive than distant metastases (p=0.008). Logistic regression model analysis of HID5/psoriasin expression in primary invasive breast tumors showed a statistically significant positive correlation between HID5/psoriasin positivity and lack of estrogen receptor (Odds ratio [OR]=6.25 and likelihood ratio [LR] p=0.001), high histologic grade (OR=20.85 LR p=0.0007), and ≧4 positive lymph nodes (OR=10.025 LR p=0.01). In other words, HID5/psoriasin positive primary invasive breast tumors are more likely to be estrogen receptor (ER) negative and high histologic grade with ≧4 positive lymph nodes. In a subset of tumor samples (156 Korean patients) HID5/psoriasin expression correlated positively with erbB2 expression (OR=5.29 LR p<0.0001), but this was not true in the combined data set possibly indicating ethnicity related differences. This study, using Fisher's exact test, also showed that, in breast cancer cells, the expression of S100A7 was associated with a higher likelihood of expression of FASN (fatty acid synthase) ($p=9.95 \times 10^{-6}$) and trefoil factor 3 (TFF3) (p=0.002), and a lower likelihood of expression of connective tissue growth factor (CTGF) (p=0.005). In addition, the expression in breast cancer cells of FASN was associated with that of TFF3 ($p=3.5 \times 10^{-6}$) and SPARC ($p=4 \times 10^{-5}$).

Since ER negative, high-grade tumors, with multiple positive lymph nodes in general tend to have worse clinical outcome, the expression of HID5/psoriasin in relation to overall and distant metastasis free survival was analyzed. Clinical follow up data was available only for a subset of patients (156 Korean patients) and this was for only up to 7 years. Based on this analysis, patients with HID5/psoriasin positive tumors had somewhat decreased >5 year overall survival; however this decrease was not statistically significant.

In summary, SAGE analysis of gene expression profiles of normal mammary epithelial cells and DCIS tumors revealed that several genes implicated in psoriasis are aberrantly expressed in high grade DCIS, with HID-5/psoriasin being one of the most abundant transcripts in these tumors. Dramatic up-regulation of HID-5/psoriasin in mammary epithelial cells in vitro is induced by growth factor deprivation, cell confluency, and lack of attachment to extracellular matrix. Because all these conditions are likely to occur in psoriatic skin lesions and high grade DCIS characterized by high proliferation rates, the high expression of HID-5/psoriasin in these cells could be due to the same signals and HID-5/psoriasin may play a role in the acquisition of apoptosis resistance of these cells.

A number of embodiments of the invention have been described. Nevertheless, it will be understood that various modifications may be made without departing from the spirit and scope of the invention. Accordingly, other embodiments are within the scope of the following claims.

What is claimed is:

1. A method of diagnosis, the method comprising:
   (a) identifying a subject suspected of having or at risk of having high-grade ductal carcinoma in situ (DCIS); and
   (b) measuring the level of psoriasin in a sample of a body fluid, a lavage, or an aspirate from the subject,
   wherein an elevated level of psoriasin in the sample, compared to a control level of psoriasin, is an indication that the subject has high grade DCIS.

2. The method of claim 1, wherein the body fluid is blood.

3. The method of claim 1, wherein the body fluid is urine.

4. The method of claim 1, wherein the lavage is a breast duct lavage.

5. The method of claim 1, wherein the aspirate is a nipple aspirate.

\* \* \* \* \*